United States Patent [19]

Moscowitz et al.

[11] 4,064,877
[45] Dec. 27, 1977

[54] SURGICAL TABLE WITH ANESTHETIC DISPENSING MEANS

[76] Inventors: George S. Moscowitz, Crane Road, Carmel, N.Y. 10512; John F. Rosen; Sarah Hiatt, both of Baldwin Place Road, Mahopac, N.Y. 10541

[21] Appl. No.: 718,788

[22] Filed: Aug. 30, 1976

[51] Int. Cl.² .......................................... A61M 17/00
[52] U.S. Cl. .................................. 128/188; 128/186; 128/185
[58] Field of Search ............... 128/188, 185, 186, 187, 128/192, 193, 194, 195, 196, 197, 198, 199, 201, 205, 206, 207, 208, 209, 210

[56] References Cited

U.S. PATENT DOCUMENTS

| 837,171 | 11/1906 | Wolfe | 128/188 |
|---|---|---|---|
| 1,512,486 | 10/1924 | Rhames | 128/188 |
| 2,199,060 | 4/1940 | Young | 128/186 |

FOREIGN PATENT DOCUMENTS 393,103  6/1933  United Kingdom ................ 128/186

*Primary Examiner*—Stephen C. Pellegrino
*Assistant Examiner*—Henry J. Recla
*Attorney, Agent, or Firm*—Bierman & Bierman

[57] ABSTRACT

An anesthetic dispenser comprising a body of generally cylindrical shape having two ends, a top on one of the ends and a barrier intermediate the ends. The barrier divides the dispenser into a receiving chamber and a dispensing section. Valve means is provided to control the flow of anesthetic from the receiving chamber to the dispensing section. The end of the section remote from the barrier is perforated to permit the anesthetic vapor to pass therethrough and a sealable filling means is in the top for introduction of the anesthetic into the receiving chamber.

The dispenser is preferably combined with a particularly described stand which is adapted for engagement with a surgical table. The entire device is primarily intended for use on small animals.

14 Claims, 3 Drawing Figures

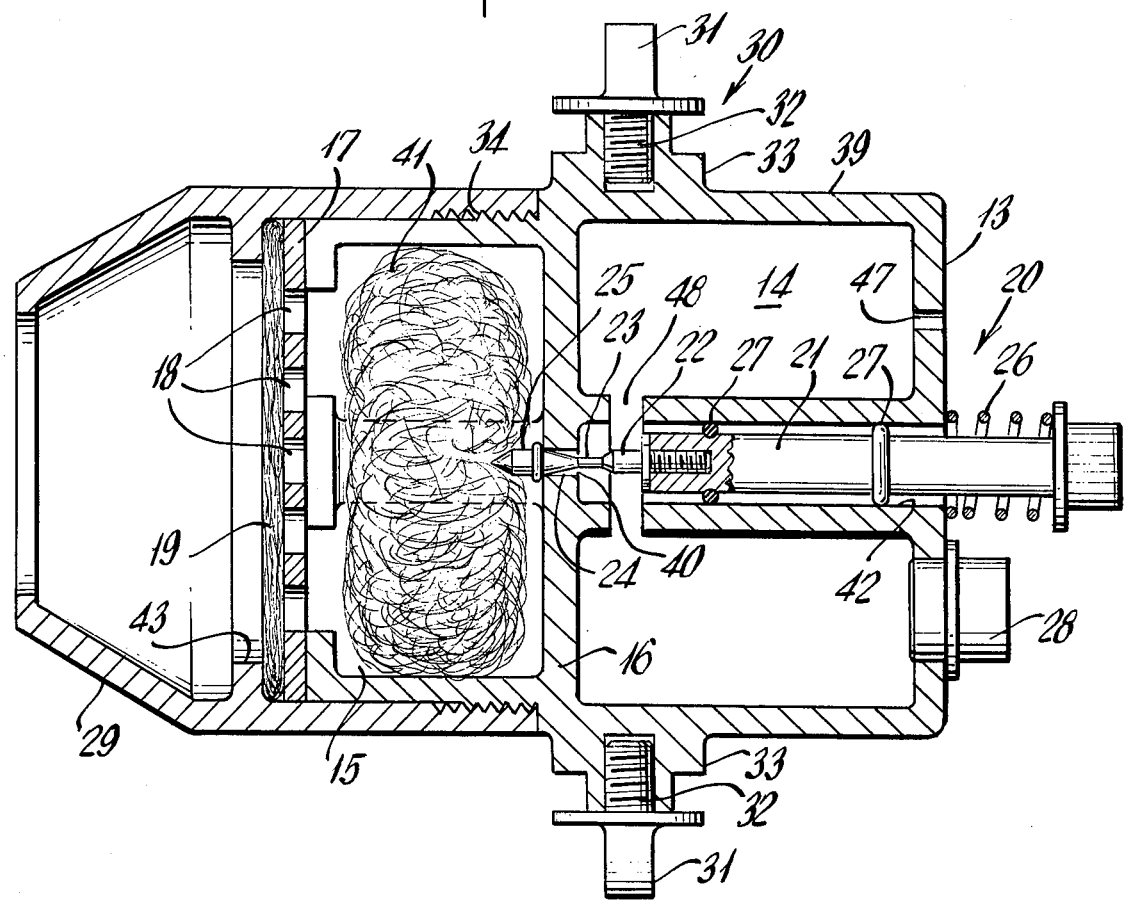
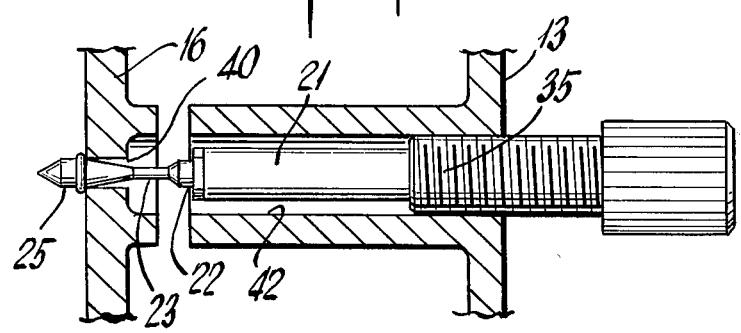

SURGICAL TABLE WITH ANESTHETIC DISPENSING MEANS

The present invention is directed to an anesthetic dispenser alone and in combination with a stand and an animal operating table. The combination of elements provides a particularly useful device for performing surgical operations on small animals, especially rodents.

The present invention comprises an anesthetic dispenser which consists of a body of generally cylindrical shape having two ends. A top is fixed on one of said ends and there is a barrier intermediate the ends which divides the dispenser into a receiving chamber and a dispensing section. Valve means is provided to control the flow of the anesthetic from the receiving chamber to the dispensing section. The end of the section remote from the barrier is perforated to permit the anesthetic vapor to pass therethrough. Sealable filling means is located in the top to permit the introduction of the anesthetic into the receiving chamber.

The valve means preferably comprises a generally cylindrical opening in the barrier and a stem having a wide portion and a narrow portion located in the opening. The wide portion is of substantially the same size as the opening and the narrow portion is of substantially smaller diameter than the opening. There is also provided means for moving the stem axially of the opening into a first and a second position. When the stem is in the first position, the wide portion is at least partially in or seals off the opening. When the stem is in the second position, the wide portion is entirely out of the opening. This permits the anesthetic to flow from the chamber into the section when the stem is in the second position, but not when the stem is in the first position.

The stem can be actuated by a plunger attached thereto and spring mounted on the top of the dispenser. The spring urges the stem into the first position.

The device is operated by merely depressing the plunger momentarily to allow the desired amount of anesthetic to flow into the dispensing section. As soon as pressure is removed from the plunger, the spring means forces it back into the first or closed position.

In a preferred form of the invention, there is provided a porous filter in the remote end of the dispensing section. It is also preferred to have a perforated support plate in the section adjacent to the filter on the side between the filter and the barrier. An absorbent material, such as cotton, can be placed in the dispensing section to absorb liquid anesthetic and permit it to evaporate at an even rate.

A preferred form of valve means has a conical portion between the narrow portion and the wide portion. This provides a third position for the stem in which the wide portion is entirely out of the opening and the conical portion is at least partially within the opening. By this means, the rate of flow of anesthetic can be controlled. As a still further variation on the valve means, the plunger extending through the opening in the top is threaded and there are corresponding threads on the inside of the opening. The plunger can then be screwed into the desired position and it will remain there without the necessity of continued pressure.

The dispenser carries diametrically opposed support means extending radially from the external portion of the body. A stand is provided which comprises two substantially parallel, vertical side portions. These side portions are spaced apart horizontally and are connected by a web which extends between them. There is a pair of dispenser slots near the upper end of the stand which receive the support means which are attached to the dispenser itself. In this manner, the dispenser is releasably suspended at an appropriate distance from the animal to be anesthetized.

The support means is preferably a pair of rods mounted on the body coupled with a pair of heads frictionally engaging the rods and movable axially thereon. Thus, the dispenser can be clamped in the dispenser slots by moving the heads axially inwardly on the rods until they engage the stand adjacent to the dispenser slots. Most preferably, the heads are threaded on the rods, thereby providing an affirmative clamping action.

It has been found particularly advantageous to place the dispenser slots at an angle to the horizontal. The dispenser can then be located both vertically and horizontally by clamping it at an appropriate place along the slots.

The dispenser and stand is placed in engagement with a surgical table. The table comprises a generally flat surface resting on a support and vertically spaced therefrom at at least one edge. The side portions of the stand are provided with a pair of table slots adjacent the lower ends thereof and the vertically spaced edge of the table is located in the slots so as to secure the dispenser and stand to the table.

It is preferable to have both edges of the table surface vertically spaced from the support. The support may be a table top, floor, etc.

Most preferably, the table is provided with a plurality of tie-downs. These comprise an elastic filament and a tie-grip having two passages therethrough. The filament passes through first one of the passages and then the other and has means near one end to prevent the end from passing through the passages. In its simplest form, the means adjacent one end can be a knot in the filament.

There are similar means spaced along the filament at various distances which are adapted to prevent the filament from passing through slits located in the table. This permits securing the extremities of the animal to the table without injuring them.

In operation, the filament is pulled partially through the second passage so as to form a loop between the first and second passages. The extremity of the animal is then placed between the loop and then the loop is tightened up. The elastic nature of the filament prevents injury to the animal and allows the extremity to be fastened down without cutting off the necessary blood supply. The remaining portion of the filament is placed in one of the slits in the table so that a knot or other means prevents sliding through the slits. This effectively holds down the animal's extremity in a position suitable for whatever surgery is to be performed.

In the accompanying drawings, constituting a part hereof, and in which like reference characters indicate like parts.

FIG. 2 is a longitudinal cross-section through the center of the dispenser; and

FIG. 3 is an enlarged sectional view of the improved form of the valve means.

Figure 1:
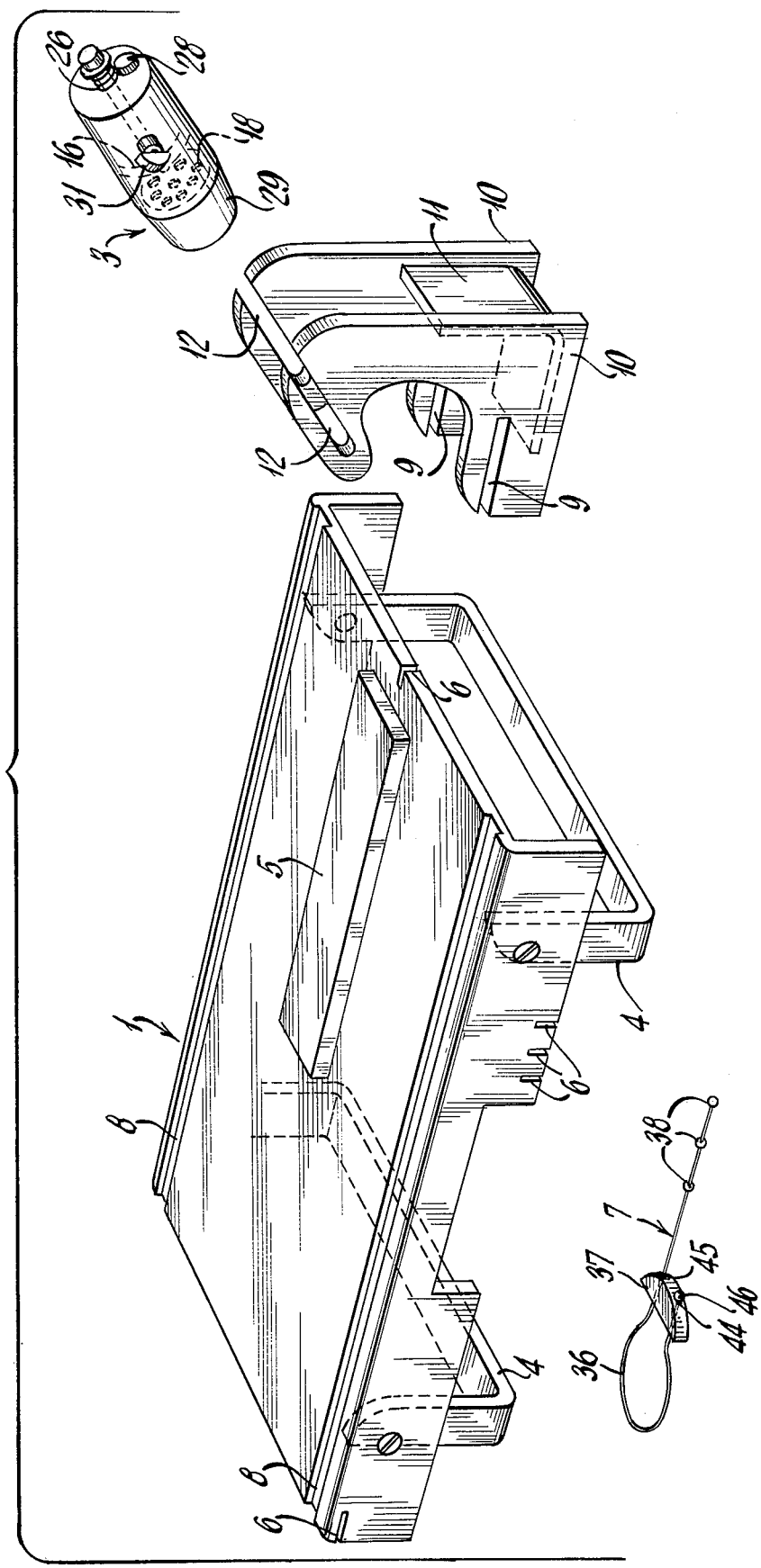
FIG. 1 is an exploded perspective view of the various portions of the invention.

The surgical unit in accordance with the present invention comprises table 1, stand 2, and anesthetic dispenser 3. Table 1 is provided with foldable legs 4 and a raised surface 5 located thereon. Slits 6 are provided at strategic locations to hold the tie-downs 7. Preferably, table 1 is provided with troughs 8 adjacent the longitudinal edges thereof. Troughs 8 are intended to carry off any biological fluids released during the surgery.

Stand 2 comprises side portions 10 spaced apart and connected by web 11. Dispenser slots 12 are located near the upper end thereof and at an angle to the horizontal. Table slots 9 are located adjacent the lower end thereof and are adapted to engage the surface of table 1.

Anesthetic dispenser 3 comprises body 39 having a top 13 and a barrier 16 which divides dispenser 3 into receiving chamber 14 and dispensing section 15. Perforated support plate 17 having holes 18 is located adjacent the lower end of dispensing section 15. Porous filter 19 is located adjacent plate 17.

Valve means 20 comprises plunger 21 affixed to stem 22 which in turn is provided with narrow portion 23, conical portion 24, and wide portion 25. Wide portion 25 is of such size that it is capable of blocking off opening 40 in barrier 16, thus preventing any flow of anesthetic from receiving chamber 14 to dispensing section 15. Stem 22 may also provide a cut-off when engaged in opening 40. Spring 26 is provided between top 13 and the head of plunger 21.

In operation, plunger 21 is depressed, thereby causing wide portion 25 to move away from the underside of barrier 16. As plunger 21 is depressed further, conical portion 24 allows an increasingly large annular space between the inner wall of opening 40 and the surface of the conical portion. At the extreme limit of axial movement of stem 22, narrow portion 23 is within opening 40. This provides the maximum flow of anesthetic from receiving chamber 14, through ports 48 and opening 40 into dispensing section 15. O-rings 27 are provided to minimize leakage. Filler cap 28 is removably inserted in top 13. The anesthetic is introduced into receiving chamber 14 at this point. Cap 28 is then placed as shown and effectively seals chamber 14 preventing escape of anesthetic. Air hole 47 aids in the flow of anesthetic from receiving chamber 14 to dispensing section 15.

Preferably, the end of dispenser 3 is provided with cone 29. This concentrates the flow of anesthetic vapor adjacent the head of the subject animal.

Supports 30 are mounted on the exterior of body 39 and are preferably diametrically opposed. They comprise heads 31 which are internally threaded. Heads 31 are threaded on to rods 32 mounted on blocks 33.

Cone 29 can be secured to body 39 by complementary cone threads 34. To secure filter 19 in position, lip 43 is provided adjacent cone 29. In the preferred form of the invention, absorbent material 41 is located within dispensing section 15.

Referring more specifically to FIG. 3, plunger 21 is provided with plunger threads 35. Plunger opening 42 is similarly threaded. This form of the device eliminates the need for spring 26 and enables the valve means 20 to be set to deliver anesthetic at any desired rate.

In use, the animal (not shown) is secured to table 1 by tie-downs 7. These comprise elastic filaments 36 passing through first passage 44 and second passage 45 in tie-grip 37. Knot 46 is provided on one end of filament 36 to prevent that end from passing through first passage 44. A loop in filament 36 is formed between first passage 44 and second passage 45 and the other end of the filament extends through second passage 45 and carries a plurality of stop means 38 thereon.

The extremity of the animal is placed within the loop between first passage 44 and second passage 45 and filament 36 is drawn tight from the free end thereof of carrying stop means 38. Since filament 36 is elastic, no injury is done to the extremity of the animal, nor is the blood supply impaired. The free end of filament 36 is then placed in one of slits 6 in table 1 with one of stop means 38 adjacent the inside thereof. This secures the extremity to the table.

While only a limited number of embodiments of this invention have been specifically described, it is, nonetheless, to be broadly construed, and not to be limited except by the character of the claims appended hereto.

What we claim is:

1. An anesthetic dispenser comprising a body of generally cylindrical shape and having two ends, a top on one of said ends, a barrier intermediate said ends and dividing said dispenser into a receiving chamber and a dispensing section, valve means adapted to control the flow of said anesthetic from said receiving chamber to said dispensing section comprising a generally cylindrical opening in said barrier, a stem in said opening, said stem having a wide portion and a narrow portion, said wide portion being at least of substantially the same size as said opening and said narrow portion being substantially smaller than said opening, means for moving said stem axially of said opening into a first position and a second position, said wide portion blocking said opening when said stem is in said first position and apart from said opening when said stem is in said second position, whereby anesthetic is permitted to flow from said chamber into said section when said stem is in said second position, the end of said section remote from said barrier being perforated to permit said anesthetic vapor to pass therethrough, said top including an opening having a sealable filling means therein for introduction of said anesthetic into said receiving chamber, diametrically opposed support means extending radially of said body, a stand comprising two substantially parallel, vertical side portions, said side portions being spaced apart horizontally and connected by a web extending therebetween adjacent the bottom end of said stand, a dispenser slot in each side portion adjacent the upper end of said stand, said slots being complementary to said support means, said support means slidably located in said dispenser slots whereby said dispenser is suspended from said stand.

2. A dispenser according to claim 1 wherein said support means comprises a pair of rods mounted on said body and a pair of heads frictionally engaging said rods and movable axially thereon whereby said dispenser can be clamped in said dispenser slots.

3. A dispenser according to claim 2 wherein said dispenser slots extend at an angle to the horizontal.

4. A surgical unit comprising a dispenser according to claim 1 and a table, said table comprising a flat surface having first and second opposed edges resting on a support and vertically spaced therefrom at at least said first edge, a table slot in each side portion adjacent the lower ends of said side portions, said slots being horizontally opposed to each other on said stand, said edge slidably located in said table slots whereby said dispenser is secured to said table.

5. A unit according to claim 4 wherein both said first and second edges of said surface are vertically spaced from said support.

6. A unit according to claim 5 wherein said table includes third and fourth opposed edges and is provided with a plurality of tie-downs, comprising slits in at least two of said first, second, third and fourth edges and an elastic filament including a tie-grip having two passages therethrough, said filament passing through both of said passages and having means adjacent one end to prevent said end from passing through said passages, further means on said filament axially spaced apart from said one end, said further means adapted to prevent said filament from sliding through said slits in said table whereby extremities of an animal can be secured without injury thereto.

7. An anesthetic dispenser comprising a body of generally cylindrical shape and having two ends, a top on one of said ends, a barrier intermediate said ends and dividing said dispenser into a receiving chamber and a dispensing section, valve means adapted to control the flow of said anesthetic from said receiving chamber to said dispensing section comprising a generally cylindrical opening in said barrier, a stem in said opening, said stem having a wide portion and a narrow portion, said wide portion being at least of substantially the same size as said opening and said narrow portion being substantially smaller than said opening, means for moving said stem axially of said opening into a first position and a second position, said wide portion blocking said opening when said stem is in said first position and apart from said opening when said stem is in said second position, whereby anesthetic is permitted to flow from said chamber into said section when said stem is in said second position, the end of said section remote from said barrier being perforated to permit said anesthetic vapor to pass therethrough, said top including an opening having sealable filling means therein for introduction of said anesthetic into said receiving chamber, said stem having a conical portion between said narrow portion and said wide portion, said stem having a third position in which said wide portion is away from said opening and said conical portion is at least partly in said opening, diametrically opposed support means extending radially of said body, a stand comprising two substantially parallel, vertical side portions, said side portions being spaced apart horizontally and connected by a web extending therebetween adjacent the bottom end of said stand, a dispenser slot in each side portion adjacent the upper end of said stand, said slots being complementary to said support means, said support means slidably located in said dispenser slots whereby said dispenser is suspended from said stand.

8. A dispenser according to claim 7 wherein there is a plunger attached to said stem, spring means on said plunger urging said stem into said first position.

9. A dispenser according to claim 7 wherein a porous filter is provided in said remote end of said section.

10. A dispenser according to claim 9 wherein a perforated support plate is located in said section, adjacent said filter, and between said filter and said barrier.

11. A dispenser according to claim 7 wherein absorbent material is in said section.

12. A dispenser according to claim 7 wherein there is a truncated cone on said section tapering in the direction away from said barrier.

13. A dispenser according to claim 12 wherein said cone is threaded onto the outer wall of said section.

14. A dispenser according to claim 7 wherein a plunger is attached to said stem and extends through a plunger opening in said top, and threads on said plunger adapted to engage complementary threads in said plunger opening.

* * * * *